United States Patent [19]

Hairston et al.

[11] Patent Number: 5,215,747
[45] Date of Patent: Jun. 1, 1993

[54] COMPOSITION AND METHOD FOR PROTECTING PLANTS FROM PHYTOPATHOGENIC FUNGI

[75] Inventors: William G. Hairston; Karen S. Arthur, both of Plano; Fred C. Rosa, Wylie, all of Tex.

[73] Assignee: Uniroyal Chemical Company, Inc., Middlebury, Conn.

[21] Appl. No.: 832,288

[22] Filed: Feb. 7, 1992

[51] Int. Cl.⁵ .............................................. A01N 63/00
[52] U.S. Cl. .................................................. 424/93 M
[58] Field of Search ..................................... 424/93 M

[56] References Cited

U.S. PATENT DOCUMENTS 4,931,398 6/1990 Kimara ............................ 424/93 M

FOREIGN PATENT DOCUMENTS 2200924 8/1988 United Kingdom ............. 424/93 M

OTHER PUBLICATIONS

Biocontrol of corn root infection in the field by seed treatment w antagonists. Kommedahl, T.; Mew, I. C. Phytopathology 1975. 65 (3): 296–300 (12 ref.).
Chemical and biological control of sunflower collar rot caused by Sclerotium rolfsii Sacc Chakraborty, Sukumar; Bhowmik, T. P. Pesticides, 19(2), 31–3, 38.
Chemical and biological control of onion white rot in muck and miner soils. Utkhede, R. S.; Rahe, J. E. Agric. Canada, Res. Sta., Summerland, BC, Canada. Plant Disease 1983. 67 (2): 153–155 (12 ref., 3 tab.).

*Primary Examiner*—John W. Rollins
*Attorney, Agent, or Firm*—Raymond D. Thompson

[57] ABSTRACT

A storage stable pre-mix composition comprising endospores of Bacillus subtilis and at least one chemical fungicide component when applied to plants, e.g., in the form of their seeds, provides enhanced protection against phytopathogenic fungi.

27 Claims, No Drawings

COMPOSITION AND METHOD FOR PROTECTING PLANTS FROM PHYTOPATHOGENIC FUNGI

BACKGROUND OF THE INVENTION

This invention relates to a composition for protecting plants, e.g., seeds of such economically important crops as cotton, peanuts, snap beans, and the like, from phytopathogenic fungi, e.g., such genera of the classes Basidiomycetes and Deuteromycetes as Rhizoctonia, Fusarium, Aspergillus, Penicillium, Ustilago, Tilletia, and so forth. More particularly, the invention herein concerns a composition containing the endospores of a microorganism capable of providing protection from phytopathogenic fungi and a chemical fungicide which is toxic to the microorganism.

The control of phytopathogenic fungi is of great economic importance since fungal growth on plants or on parts of plants, e.g., fruits, blossoms, foliage, stems, tubers, roots, etc., inhibits production of foliage, fruit or seed and reduces the overall quantity and quality of the harvested crop. The continuous economic toll taken by phytopathogenic fungi establishes a continuing need to develop new, more effective fungicides which possess curative, preventative and systemic action to protect cultivated plants and the seeds from which they develop. Those requirements must be accomplished without any significant adverse side effects to the plants of the desired crops.

Compositions containing dried bacteria and agricultural chemicals have been employed to pre-treat or pre-inoculate seeds. However, these compositions have sometimes exhibited reduced bacterial activity over time, presumably as a result of the degradative effects of the chemical component on the biological component. Such compositions have even been found to lack virtually all bacterial activity despite having been formulated with an adequate quantity of bacteria. For this reason, it has been the practice to apply a chemical fungicide such as captan, thiram, carboxin, metalaxyl, quintozene (PCNB), and the like to the seed well in advance of planting, but to only apply *Bacillus subtilis* endospores, a known seed inoculant (e.g., Quantum-4000® HB biological inoculant available from Gustafson, Inc., Plano, Tex.), to the seed just before planting on the premise that a reduced period of exposure of the *Bacillus subtilis* endospores to the chemical fungicide will minimize any loss of bioeffectiveness of the spores.

SUMMARY OF THE INVENTION

It has now been surprisingly discovered that a premix composition comprising *Bacillus subtilis* and chemical fungicide will experience little loss of bio-effectiveness even after relatively long periods of storage, e.g., from 2 to 12 months and even longer.

Accordingly, the present invention provides a storage-stable pre-mix composition which comprises at least one strain of *Bacillus subtilis* in substantially uniform admixture with at least one chemical fungicide and a method for protecting a plant from phytopathogenic fungi to which the plant is susceptible which comprises contacting the plant with a fungal-protecting amount of the foregoing composition.

The plant treatment composition of this invention has been found to provide a greater degree of protection from pathogenic fungi than would be expected from application of either the *Bacillus subtilis* endospores or the chemical fungicide alone. In the case of application to seed, it is believed that the chemical fungicide component of the composition functions immediately upon planting to protect the seed from attack by soil-borne phytopathogenic fungi. Later, as the seed germinates and the plant roots develop, the bacterial component competes for space on the surface of the developing roots thus extending the duration of protection from fungal attack and providing the plant with the opportunity to become more firmly and vigorously established. Whatever the actual protective mechanism(s) involved, the fact remains that the pre-mix composition of this invention when applied to a plant provides an unexpectedly greater degree of protection from fungal attack, observed in terms of increased crop yields, than that which would be expected from the use of the bacterial component or the chemical fungicide component by itself.

The term "plant" as used herein is to be understood in its widest sense and includes seeds, roots, stems, leaves, and so forth.

DESCRIPTION OF THE PREFERRED EMBODIMENTS

The *Bacillus subtilis* endospores employed in the composition of this invention are advantageously of the relatively thick walled variety. Such endospores are commercially available, e.g., aforementioned Quantum-4000® biological inoculant of Gustafson, Inc., Plano, Tex. The thick-walled strain of *Bacillus subtilis* provides effective protection against a number of strains of common phytopathogenic fungi including those of the Rhizoctonia and Fusarium species and is an excellent colonizer of cotton seedlings in the presence of many chemical seed treatment fungicides. Cells or spores of other biological control agents can also be included.

The chemical fungicide component(s) of the composition of the present invention are well known with many being commercially available. Useful chemical fungicides are described in "The Pesticide Manual", C. R. Worthing, ed., 9th ed. (British Crop Protection Council, 1991) the contents of which are incorporated by reference herein.

In a preferred embodiment of the composition herein, a combination of chemical fungicides is employed, e.g., a chemical fungicide component (a) which is effective against one or more soil or air-borne fungal pathogens of the order Peronosporales (known to cause seed or seedling diseases such as Pythium, Phytophthora and downy mildew) and a chemical fungicide component (b) which is effective against one or more soil-borne fungal pathogens of any of the classes of Basidiomycetes and Deuteromycetes such as Rhizoctonia, Fusarium, Aspergillus, Penicillium, Ustilago and Tilletia. In some cases, a single chemical fungicide may satisfy the functions of both fungicide components.

Examples of fungicide component (a) include metalaxyl (N-(2,6-dimethylphenyl)-N-methoxyacetyl)-alanine methyl esther: British Patent No. 1,500,581), oxadixyl (2-methoxy-N-(2-oxo-1,3-oxazolidin-3yl)acet-2',6'-xylidide: British Patent No. 2,058,059), etridiazole (5-ethoxy-3-trichloromethyl-1,2,4-thiadiazole: U.S. Pat. Nos. 3,260,588 and 3,260,726), captan (cis-N-trichloromethylthio-4-cyclohexene-1,2-dicarboximide: U.S. Pat. Nos. 2,553,770; 2,553,771 and 2,553,776), thiram (tetramethylthiuram disulfide: U.S. Pat. No. 1,972,961), maneb (manganese ethylenebis (dithiocarbamate): U.S. Pat. Nos. 2,504,404 and 2,710,822), mancozeb (a complex of zinc and maneb containing 20% manganese and 2.55% zinc: U.S. Pat. Nos. 3,379,610 and 2,974,156), and the like.

Examples of fungicide component (b) include carboxin (5,6-dihydro-2-methyl-1,4-oxathi-ine-3-carboxanilide: U.S. Pat. Nos. 3,249,499, 3,393,202 and 3,454,391), quintozene (pentachloronitrobenzene), chloroneb (1,4-dichloro-2,5-dimethoxybenzene: U.S. Pat. No. 3,265,564), thiophanate-methyl (dimethyl 4,4'-(o-phenylene) bis(3-thioallophanate)), captan, thiram, maneb, mancozeb, dicloran (2,6-dichloro-4-nitroaniline: British Patent No. 845,916), thiabendazole (2-(1,3-thiazol-4-yl)benzimidazole: U.S. Pat. No. 3,017,415), imazalil ( ($\pm$)-allyl 1-(2,4-dichlorophenyl=2-imidazol-1-ylethyl ether)), triadimenol ( ( 1RS, 2RS; 1RS, 2SR)-1-(4-chlorophenoxy)-3,3 dimethyl-1-(1H-1,2,4-triazol-1-yl)butan-2-ol: German Patent No. 2,324,010).

In the foregoing preferred composition, an especially preferred example of fungicide component (a) is metalaxyl, a residual fungicide with systemic properties suitable for preventive and curative control of diseases caused by air- and soil-borne Oomyetes. It is recommended for use in cotton against seed and seedling decay caused by *Phythium ultimum*, in potatoes against *Phytophthora infestans*, in grape vines against *Plasmopara humuli* and in lettuces against *Bremia lactucae*. An especially preferred example of fungicide component (b) is pentachloronitrobenzene (PCNB), a fungicide of specific use for seed and soil treatment, effective against *Tilletia caries* of wheat, Botrytis, Rhizoctonia and Sclerotinia spp. on brassicas, vegetable and ornamental crops.

The invention is, of course, inclusive of other chemical fungicides. Typical examples of other chemical fungicide components which can be included in the composition of this invention include thiram, which is a fungicide suitable for application to foliage or fruit to control Botrytis spp., *Bremia lactucae* and *Venturia pirinia* on soft fruit, vegetables, ornamentals, lettuces and pears. Thiram can also be used as a seed treatment, with or without added insecticide or other fungicide, in vegetables, maize and ornamentals.

Further illustrative examples of useful chemical fungicides include captan, a fungicide useful for controlling fungal diseases of many fruit, vegetable and ornamental crops including *Venturia inaequalis* of apple, *Venturia pirina* of pear, and Phythium spp. of corn. Another example of a chemical fungicide which can advantageously be employed in the composition of this invention is carboxin, a systemic fungicide useful for the treatment of cereal seed against smuts and bunts and when combined with cofungicides, for the control of most other soil-borne fungi and against Rhizoctonia spp. of cotton, groundnuts, and vegetables.

The optimum amounts of *Bacillus subtilis* endospores and the optimum amount(s) and type(s) of chemical fungicides(s) employed in the plant treatment composition herein for a particular application can be readily determined by those skilled in the art. In general, the active ingredient portion of a composition in accordance with this invention can contain from about 0.001% to about 50% by weight, and preferably from about 0.01% to about 30% by weight, of *Bacillus subtilis* endospores, the balance of the active ingredient portion being made up of one or more chemical fungicides. In the preferred composition employing at least one each of the aforementioned types of fungicides (a) and (b), the weight ratios of fungicides (a) and (b) can vary from about 1:500 to about 500:1 and preferably from about 1:100 to about 100:1.

The composition of the present invention can further comprise one or more biologically inert components, e.g., carrier materials such as talc, gypsum, kaolin, attapulgite, wood flour, ground corn cob, and the like, stickers or binders such as ethylene glycol, mineral oil, polypropylene glycol, polyvinylacetate, nutrients, plant growth hormones, and the like.

The compositions of this invention can be formulated as a powder by mixing together all the dry components, including any carrier and/or other additive(s) which may be utilized until a homogeneous mixture is formed. A sticker, if employed, may then be added and the entire mass mixed again until it has become essentially uniform in composition.

In the case of a liquid formulation, organic solvents such as xylene, methanol, ethylene glycol and mineral oil can be used as diluting agents and such surface active agents as, for example, calcium dodecylbenzenesulfonate, polyglycol ether, ethoxylated alkyl phenol and alkyl aryl sulfonates can be utilized.

In the case of granular formulations, the carrier can be of the inorganic or organic variety such as attapulgite, montmorillonite, bentonite, wood flour, corn cob grits, starch, cellulose, bran, etc. Stickers such as mineral oil, lignosulfonate, polyvinyl alcohol or sucrose can be employed to maintain granular integrity.

Moreover, the compositions of this invention can be used together with one or more other pesticidal materials such as insecticides, for example, organochlorine compounds such as lindane (1,2,3,4,5,6-hexachlorocyclohexane (gamma isomer)); organophosphoric esters such as diazinon (0,0-diethyl 0-2-isopropyl-6-methylpyrimidin-4-yl phosphorothioate), isazofos (0-5-chloro-1-isopropyl-1H-1,2,4-triazol-3-yl 0,0-diethyl phosphorothioate), thiofanox (1-(2,2-dimethyl-1-methylthiomethylpropylideneaminooxy)-N-methylformamide), and the like; and carbamates such as carbofuran (2,3-dihydro-2,2-dimethylbenzofuran-7-yl methylcarbomate), mercaptodimethur (3,5-dimethyl-4-(methylthio) phenol methyl carbamate), bendiocarb (2,2-dimethyl-1,3-benzodioxol-4-yl methylcarbamate), and the like; and repellants such as anthraquinone, thioanthraquinone, benzathrone, ziram (zinc bis(dimethyldithiocarbomate)) and diphenylguanidine, and the like.

In general, the *Bacillus subtilis* endospore component of the composition of this invention will retain at least about 50, and preferably at least about 70, percent of its original viability after storage of the composition for a period of up to about 36 months. The *Bacillus subtilis* endospore can also retain at least about 50 percent of its original viability after storage of the composition for a period of up to about 48 months.

The method of this invention comprises applying to plants a fungicidally effective amount of the composition herein. Although the composition can be applied to any portion of the plants such as foliage, it is especially effective as a seed dressing. When employed as a seed dressing, the composition is generally applied to the seed at a rate of from about 125 to about 2000 grams, and preferably at a rate of from about 250 to about 750 grams per 100 kilograms of seed. The method is effective on all agronomic and vegetable crops such as cotton, peanut or snap beans.

As the following examples demonstrate, plant protecting compositions in accordance with this invention exhibit unexpectedly enhanced protection against phytopathogenic fungi. Quantum 4000 ® HB (Gustafson, Inc.) initially containing at least about $1.1 \times 10^{10}$ viable endospores of Bacillus subtilis) was employed as the biological component of the compositions illustrated in the examples. The chemical fungicides used in the compositions of the examples were Apron TM (metalaxyl from Ciba-Geigy Corp.) and Terraclor ® (PCNB from Uniroyal Chemical Company Inc.).

EXAMPLE 1

For hopper box dry treatment of cotton seed, the rates of application are 5.0 and 7.5 grams of composition per kilogram of seed. For the seed treatments shown in Table 1, infra, 113.4 g of seed were treated. Thus, for the 5.0 g/kg application rate, 0.57 g of treatment composition was applied to 113.4 g of seed in a paper bag and shaken vigorously to achieve good coverage of the seed. For the 7.5 g/kg application rate, 0.85 g of treatment composition were applied to 113.4 g of seed.

To evaluate and compare the efficacy of chemical and biological agents, alone and in combination, in controlling the soilborne damping off organism Rhizoctonia solani AG4, the following screening procedure was employed. An isolate of Rhizoctonia solani AG4 (RS AG4) from cotton was grown for a seven day period at 28° C. on potato dextrose agar amended with 50 ppm streptomycin sulfate. One petri plate of RS AG4 was blended with 600 ml of water. After securing a homogeneous blend, the inoculum was incorporated into a sterilized 1:1 by weight sand to loam soil mixture at an RS AG4 concentration of 1.6% volume/weight ratio to soil. Uniformity of the mixture was insured employing a cement mixer.

Flats measuring 304.8 mm×457.2 mm×63.5 mm were filled with 12.70 kg of the inoculated soil and prepared for planting of seed treatments. Seed treatments were planted utilizing a randomized block design of 5 replications per seed treatment with 20 seed planted per replication. Five treatments were planted per flat in a linear arrangement and watered with 600 ml of water. The flats were then placed in a 25° C. walk-in growth room with a 10 hour photoperiod. Data was collected with an initial emergence count of seedlings followed by counts of surviving seedlings.

The efficacy data presented in Table 1 below was obtained for biological seed treatment, i.e., Bacillus subtilis endospores alone at 1.0% by weight (Treatment No. 2), chemical fungicide seed treatment alone containing 6.25% Apron TM and 25% Terraclor ® (Treatment No. 3) and biological/chemical treatment in accordance with the invention (Apron-Terraclor-Bacillus subtilis containing 4.25% Apron TM, 16.67% Terraclor ® and 1.0% Bacillus subtilis, not less than $1.2 \times 10^{10}$ spores per gram; Treatment No. 4). For comparison purposes, an untreated control was provided (Treatment No. 1). The results were as follows:

TABLE 1

| SEED TREATMENT | % EMERGENCE AT DAY 7 | SURVIVAL (DAYS) | | | | |
|---|---|---|---|---|---|---|
| | | 11 | 13 | 15 | 18 | 21 |
| 1. Untreated Control | 91.0 | 53.0 | 40.0 | 38.0 | 31.0 | 24.0 |
| 2. Bacillus subtilis endospores at 7.5 g/kg | 90.0 | 78.0 | 66.0 | 52.0 | 38.0 | 33.0 |
| 3. Apron-Terraclor at 5.0 g/kg | 94.0 | 87.0 | 88.0 | 82.0 | 65.0 | 56.0 |
| 4. Apron-Terraclor-Bacillus subtilis endospores at 7.5 g./kg | 94.0 | 96.0 | 96.0 | 91.0 | 84.0 | 76.0 |

As these data show, Treatment Nos. 2–4 resulted in significantly greater seedling survival at the end of 21 days than in the case of the untreated seeds. However, as between treatment Nos. 2–4, that which was carried out in accordance with the present invention, i.e., Treatment No. 4, resulted in substantially greater seedling survival than the solely biological approach (Treatment No. 2) and the solely chemical approach (Treatment No. 3) to seed protection.

EXAMPLE 2

Example 1 was substantially repeated except that Bacillus subtilis endospores were applied at a level of 5.00 g/kg oz/cwt. The results are shown in Table 2 as follows:

TABLE 2

| SEED TREATMENT | % EMERGENCE AT DAY 7 | SURVIVAL (DAYS) | | | | |
|---|---|---|---|---|---|---|
| | | 11 | 13 | 15 | 18 | 21 |
| 5. Untreated Control | 91.0 | 53.0 | 40.0 | 38.0 | 31.0 | 24.0 |
| 6. Bacillus subtilis endospores at 5.0 g/kg | 84.0 | 57.0 | 51.0 | 43.0 | 33.0 | 23.0 |
| 7. Apron-Terraclor at 5.0 g/kg | 94.0 | 87.0 | 88.0 | 82.0 | 65.0 | 56.0 |
| 8. Apron-Terraclor-Bacillus subtilis endospores at 5.0 g/kg | 96.0 | 95.0 | 95.0 | 94.0 | 91.0 | 81.0 |

After 21 days, cotton seedlings grown in RS AG4 infested soils were submitted to severe disease challenge as evidenced by the untreated control (Treatment No. 5) having only 24% survived seedlings. The biological treatment alone (Treatment No. 6) resulted in 23% survived seedlings whereas the chemical treatment (Treatment No. 7) resulted in disease control with 56% survival of seedlings. However, when the seeds were treated with a combination of chemical and biological agents in accordance with this invention the level of healthy seedlings increased to a significantly greater level of 81%.

EXAMPLE 3

Cotton seed (DP90, containing an average of about 4900 seeds per pound) was treated in various ways as summarized in Table 3, infra, and evaluated in the field.

Treatment No. 9 was applied by placing 100 g of seed in a 500 ml screw-cap glass jar. 1.5 ml of water was added dropwise to the seed with mixing. The jar was capped and shaken vigorously for 1 minute. 0.5 g of 500 mesh talc was added to the moistened seed and the seed was again shaken vigorously for 1 minute to uniformly coat the seed. The seed was then air dried for 1 hour and packaged.

Treatment No. 10, Apron ™-Terraclor ® at 2.5 g/kg seed, was prepared by placing 454 g seed treated with the commercially available mixture of these chemical fungicides in a one liter glass container. 1.13 g of the mixture was added to the seed and the jar was shaken vigorously for one minute to uniformly coat the seed. 100 g of this treated seed was overtreated with 1.5 ml water and 0.5 g talc as described in Treatment No. 9.

Treatment No. 11, Apron ™-Terraclor ® at 2.5 g/kg seed and *Bacillus subtilis* endospores (4.6×10$^{10}$ spores/g) at 1.3 g/kg seed, was obtained by placing 100 g of the Apron Terraclor treated seed in a 500 ml screw-cap glass jar. 1.77 g of powder of 4.6×10$^{10}$ *Bacillus subtilis* spores/g and 5.04 g of talc (500 mesh) were dry-mixed with a mortar and pestle. 1.5 ml of water was added first to the 100 g of seed as in Treatment No. 9. To the moistened seed, 0.5 g of the powder and talc mixture was added. The seed was then vigorously shaken for 1 minute and allowed to air dry for 1 hour.

Treatment No. 12, *Bacillus subtilis* endospores at 1.3 g/kg seed, was obtained by placing 100 g of untreated seed in a jar and adding 1.5 ml of water to moisten as in Treatment No. 9. 0.5 g of the *Bacillus subtilis* endospores/talc powder from Treatment No. 11 was added to the moistened seed. The seed was then vigorously shaken for one minute and allowed to dry for one hour.

Four 100-seed samples from each of the four treatments were counted out. The seed was planted by hand in a furrow 76.2 mm. deep and 6.1 m. long. Each 100 seed sample was planted using a randomized complete block statistical design. Stand counts were made of the number of emerged seedlings on day 18 following planting.

TABLE 3

| SEED TREATMENT | % EMERGENCE AT DAY 17 | % FINAL STAND AT DAY 31 |
|---|---|---|
| 9. Talc at 5.0 g/kg (control) | 39.25 | 36.50 |
| 10. Apron-Terraclor at 2.5 g/kg | 42.25 | 48.50 |
| 11. Apron-Terraclor at 2.5 g/kg *Bacillus subtilis* endospores at 1.3 g/kg and Talc at 3.7 g/kg | 58.00 | 56.50 |
| 12. *Bacillus subtilis* endospores at 1.3 g/kg and Talc at 3.7 g/kg | 30.00 | 34.24 |

As these data show, the plant protecting composition of this invention (Treatment No. 11) significantly outperformed the other treatments (Nos. 9, 10 and 12).

EXAMPLE 4

The same treatments as in Example 3 were evaluated in a growth chamber in sterilized soil inoculated with the pathogen *Rhizoctonia solani*. Five replicates of 20 seeds each were randomized and planted in flats containing the inoculated soil. The growth chamber was an environmentally-controlled room which had a constant temperature of 25° C., 12 hours of simulated daylight and 12 hours of darkness each day.

The results of the growth chamber plantings are set forth in Table 4 as follows:

TABLE 4

| SEED TREATMENT | % EMERGENCE AT DAY 6 | % SURVIVAL AT DAY 10 | % SURVIVAL AT DAY 17 |
|---|---|---|---|
| 13. Talc at 3.7 g/kg (control) | 97 | 79 | 2 |
| 14. Apron-Terraclor at 2.5 g/kg | 93 | 94 | 28 |
| 15. Apron-Terraclor at 2.5 g/kg *Bacillus subtilis* endospores at 1.3 g/kg and Talc at 3.7 g/kg | 8 | 99 | 48 |
| 16. *Bacillus subtilis* endospores at 1.3 g/kg and Talc at 3.7 g/kg | 93 | 82 | 24 |

These results demonstrate the decidedly improved survival of seedlings employing the composition of this invention (Treatment No. 15) compared to the other treatments (Treatment Nos. 13, 14 and 16).

EXAMPLE 5

To evaluate the storage stability of a plant protecting composition in accordance with this invention, an Apron ™-Terraclor ®-*Bacillus subtilis* endospore composition (4.25% Apron, 16.67% Terraclor and 1.0% *Bacillus subtilis* endospores, not less than 1.2×10$^{10}$ viable spores per gram) was subjected to an accelerated aging test of 30 days at 40° C.±2° C., a period simulating a storage length of about six months. During the test, 20 g of the composition was stored in a beaker and maintained under a constant pressure of 25 g/cm$^2$ by means of a weight. The results of the test are set forth in Table 5 as follows:

TABLE 5

| ACCELERATED STORAGE STABILITY | | |
|---|---|---|
| Component | Initial Value at Ambient Conditions | Value After 30 days at 40 C. ± 2 °C. |
| Apron | 4.84 | 4.74 |
| Terraclor | 16.79 | 16.66 |
| *Bacillus subtilis* endospores | 1 × 10$^{10}$ viable spores/g | 7.6 × 10$^{10}$ viable spores/g |

What is claimed is:

1. A storage-stable pre-mix composition which comprises the endospores of *Bacillus subtilis* in substantially uniform admixture with at least one chemical fungicide component.

2. The composition of claim 1 containing relatively thick-walled endospores of *Bacillus subtilis*.

3. The composition of claim 1 further comprising cells or spores of other biological control agents.

4. The composition of claim 1 containing a chemical fungicide component (a) which is effective against a fungal pathogen of the order Peronosporales, and a chemical fungicide component (b) which is effective against a fungal pathogen selected from the group consisting of the class Basidiomycetes and Deuteromycetes.

5. The composition of claim 4 wherein chemical fungicide component (a) is selected from the group consisting of metalaxyl, oxadixyl, etridiazole, captan, thiram, maneb and mancozeb.

6. The composition of claim 4 wherein chemical fungicide component (b) is selected from the group consisting of carboxin, quintozene, chloroneb, thiophanatemethyl, captan, thiram, maneb, mancozeb, dicloran, thiabendazole, imazalil and triadimenol.

7. The composition of claim 4 wherein chemical fungicide component (a) is metalaxyl and chemical fungicide component (b) is quintozene.

8. The composition of claim 4 wherein the weight ratio of chemical fungicide component (a) and chemical fungicide component (b) ranges from about 1:500 to about 500:1, respectively.

9. The composition of claim 8 wherein the weight ratio of chemical fungicide component (a) and chemical fungicide component (b) ranges from about 1:100 to about 100:1, respectively.

10. The composition of claim 4 wherein chemical fungicide component (b) is effective against at least one of Rhizoctonia, Fusarium, Aspergillus, Penicillium, Ustilago or Tilletia.

11. The composition of claim 1 wherein the *Bacillus subtilis* endospores retain at least about 50 percent of their initial viability after storage of the composition for a period of up to about 48 months.

12. The composition of claim 1 wherein the *Bacillus subtilis* endospores retain at least about 70 percent of their initial viability after storage of the composition for a period of up to about 36 months.

13. The composition of claim 1 wherein the endospores of *Bacillus subtilis* are present in an amount ranging from about 0.001% to about 50% by weight of said composition.

14. The composition of claim 13 wherein the endospores of *Bacillus subtilis* are present in an amount ranging from about 0.01% to about 30% by weight of said composition.

15. A method for protecting a plant from phytopathogenic fungi to which the plant is susceptible which comprises contacting the plant with an effective amount of a storage stable pre-mix composition comprising the endospores of *Bacillus subtilis* in substantially uniform admixture with at least one chemical fungicide component.

16. The method of claim 15 wherein foliage of the plant is contacted with the composition.

17. The method of claim 15 wherein the plant is in the form of its seed.

18. The method of claim 17 wherein the seed is that of cotton, peanut or snap beans.

19. The method of claim 15 wherein the plant is that of a root.

20. The method of claim 15 wherein the plant is an agronomic or vegetable crop.

21. The method of claim 15 wherein the composition contains relatively thick-walled endospores of *Bacillus subtilis.*

22. The method of claim 15 wherein the composition further comprises cells or spores of other biological control agents.

23. The method of claim 15 wherein the composition contains a chemical fungicide component (a) which is effective against a fungal pathogen of the order Peronosporales, and a chemical fungicide component (b) which is effective against a fungal pathogen selected from the group consisting of the class Basidiomycetes (and) Deuteromycetes.

24. The method of claim 23 wherein chemical fungicide component (b) is effective against at least one of Rhizoctonia, Fusarium, Aspergillus, Penicillium, Ustilago or Tilletia.

25. The method of claim 23 wherein chemical fungicide component (a) is selected from the group consisting of metalaxyl, oxadixyl, etridiazole, captan, thiram, maneb and mancozeb.

26. The method of claim 23 wherein chemical fungicide component (b) is selected from the group consisting of carboxin, quintozene, chloroneb, thiophanatemethyl, captan, thiram, maneb, mancozeb, dicloran, thiabendazole, imazalil and triadimenol.

27. The method of claim 23 wherein chemical fungicide component (a) is metalaxyl and chemical fungicide component (b) is quintozene.

* * * * *